US00PP12344P2

(12) United States Plant Patent
Jorna

(10) Patent No.: US PP12,344 P2
(45) Date of Patent: Jan. 8, 2002

(54) NEW GUINEA IMPATIENS PLANT NAMED 'TAMAR CANDY CANE'

(75) Inventor: Anita Jorna, Maasland (NL)

(73) Assignee: Pides Goldstock Breeding B.V., Maasland (NL)

( * ) Notice: Subject to any disclaimer, the term of this patent is extended or adjusted under 35 U.S.C. 154(b) by 0 days.

(21) Appl. No.: 09/712,347

(22) Filed: Nov. 15, 2000

(51) Int. Cl.[7] ..... A01H 5/00
(52) U.S. Cl. ..... Plt./318

(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Tamar Candy Cane', characterized by its light pink and red bi-colored flowers; freely flowering habit with flowers positioned above or beyond the foliage; upright, somewhat outwardly spreading, rounded, uniform and compact plant habit; freely branching growth habit; and dark green leaves.

1 Drawing Sheet

BACKGROUND OF THE INVENTION

The present Invention relates to a new and distinct cultivar of New Guinea Impatiens plant, botanically known as *Impatiens hawkeri*, and hereinafter referred to by the cultivar name Tamar Candy Cane.

The new Impatiens is a product of a planned breeding program Inventor in Maasland, The Netherlands. The objective of the breeding program is to develop new Impatiens cultivars with uniform plant habit and attractive flower and foliage colors.

The new Impatiens originated from a cross made by the Inventor in 1997 of the Inventor's proprietary *Impatiens hawkeri* selection code number 944106, not patented, as the male, or pollen parent, with the Inventor's proprietary *Impatiens hawkeri* selection code number 942606, not patented, as the female, or seed parent. The cultivar Tamar Candy Cane was discovered and selected by the Inventor as a flowering plant within the progeny of the stated cross in a controlled environment in Maasland, The Netherlands in 1997.

Asexual reproduction of the new cultivar by terminal cuttings taken at Maasland, The Netherlands, has shown that the unique features of this new Impatiens are stable and reproduced true to type in successive generations.

SUMMARY OF THE INVENTION

The following traits have been repeatedly observed and are determined to be the unique characteristics of 'Tamar Candy Cane'. These characteristics in combination distinguish 'Tamar Candy Cane' as a new and distinct Impatiens cultivar:

1. Light pink and red bi-colored flowers.
2. Freely flowering habit with flowers positioned above or beyond the foliage.
3. Upright, somewhat outwardly spreading, rounded, uniform and compact plant habit.
4. Freely branching growth habit.
5. Dark green leaves.

Plants of the new Impatiens differ from plants of the parent selections in leaf and flower color.

In side-by-side comparisons conducted by the Inventor in Maasland, The Netherlands, plants of the new Impatiens differ from plants of the cultivar Pago Pago, disclosed in U.S. Plant Pat. No. 9,143, in flower color and in the following characteristics:

1. Plants of the new Impatiens flower earlier than plants of the cultivar Pago Pago.
2. Plants of the new Impatiens have larger flowers than plants of the cultivar Pago Pago.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new Impatiens. The photograph comprises a top perspective view of a typical flowering plant of 'Tamar Candy Cane' grown in a 12.5-cm container.

DETAILED BOTANICAL DESCRIPTION

The cultivar Tamar Candy Cane has not been observed under all possible environmental conditions. The phenotype may vary somewhat with variations in environment such as temperature, light intensity, water status and fertility level, without, however, any variance in genotype. The following observations and measurments describe plants grown in Maasland, The Netherlands, during the early autumn, under commercial practice in a glass-covered greenhouse. Plants used in the following description were about 10 to 12 weeks old from planting rooted cuttings and grown in 12.5-cm containers with one plant per container.

In the following description, color references are made to The Royal Horticultural Society Colour Chart except where general terms of ordinary dictionary significance are used.

Botanical classification: *Impatiens hawkeri* cultivar Tamar Candy Cane.

Commercial classification: New Guinea Impatiens cultivar Tamar Candy Cane.

Parentage:

*Male parent.*—Inventor's proprietary *Impatiens hawkeri* selection code number 944106, not patented.

*Female parent.*—Inventor's proprietary *Impatiens hawkeri* selection code number 942606, not patented.

Propagation:

*Type cutting.*—Terminal cuttings.

*Time to initiate roots.*—Summer: About 5 to 7 days at 19 to 20° C. Winter: About 6 to 8 days at 19 to 20° C.

*Time to produce a rooted cutting or liner.*—Summer: About 14 to 19 days at 19 to 20° C. Winter: About 14 to 21 days at 19 to 20° C.

*Root description.*—Numerous, fibrous, and freely branching.

Plant description:

*General appearance.*—Upright, somewhat outwardly spreading, rounded, uniform and compact plant habit. Appropriate for 10 to 25-cm containers; multiple plants are typically planted in larger containers.

*Growth and branching habit.*—Freely branching with about 8 lateral branches at the base. Pinching, that is, removal of the terminal apices, is typically not required. Moderately vigorous.

*Crop time.*—From a rooted cutting, about 10 to 12 weeks are required to produce finished flowering plants in 12-5-cm containers.

*Plant height.*—About 15.2 cm.

*Plant diameter.*—About 36.5 cm.

*Lateral branches.*—Length: About 14.3 cm. Diameter: About 8.5 mm. Internode length (lower internodes): About 3.8 cm. Color: Close to 59A.

*Foliage description.*—Arrangement: Opposite or whorled. Length: About 8.4 cm. Width: About 3.4 cm. Shape: Broadly elliptic. Apex: Acute to acuminate. Base: Attenuate. Margin: Serrulate with ciliation. Texture: Leathery; upper and lower surfaces, pubescence on veins. Aspect: Somewhat arching. Color: Young foliage, upper surface: Close to 147A with dark red, close to 57A, undertones. Young foliage, lower surface: Close to 59A. Fully expanded foliage, upper surface: Darker than 147A. Fully expanded foliage, lower surface: Lighter than 59A. Midvein, upper surface: Close to 59A to 53A. Midvein, lower surface: Close to 59A to 53A. Petiole: Length: About 1.7 cm. Diameter: About 2.5 mm. Color: Close to 53A.

Flower description:

*Flower type and flowering habit.*—Single light pink and red bi-colored flowers. Freely flowering, usually about 9 flowers and flower buds per lateral branch. Flowers positioned above and beyond the foliage and typically face upward or outward. Flowers cupped when opening then mostly flat when opened. Flowers roughly rectangular in shape. Flowers last about 7 to 14 days on the plant depending on temperature and weather conditions. Petals self-cleaning; gynoecium persistent. Flowers not fragrant.

*Flowering season.*—Year-round under greenhouse conditions. In the garden, flowering from spring until fall.

*Flower length.*—About 5.1 cm.

*Flower width.*—About 4.8 cm.

*Flower depth.*—About 1.3 cm.

*Flower buds (just before opening).*—Rate of opening: From showing color to fully open flower, typically about 2 to 3 days depending on temperature. Length: About 1.7 cm. Diameter: About 1.3 cm. Shape: Ovoid. Color: 45B.

*Petals.*—Quantity: Single, five per flower. Length: Banner petal: About 2.8 cm. Lateral petals: About 2.7 cm. Base petals: About 3 cm. Width: Banner petal: About 3.4 cm. Lateral petals: About 2.7 cm. Base petals: About 3.3 cm. Shape: Roughly orbicular. Apex: Emarginate. Base: Attenuate. Margin: Entire. Texture: Smooth; velvety. Color: When opening and fully opened, upper surface: Banner petal: Central apical splotch, 45A to 45B; surrounded by 56A to 56D. Lateral and base petals: Central stripe and base, 45A to 45B; surrounded by 56A and 56D. When opening and fully opened, lower surface: Central stripe and base, 45A to 45C; surrounded by 56A to 56D.

*Spur.*—Length: About 5.9 cm. Diameter: About 2 mm at flower; apex, about 1 mm. Color: Proximally, 145D; distally, 144C to 144B.

*Peduncles.*—Length: About 5.25 cm. Diameter: About 1.5 mm. Strength: Strong, flexible. Aspect: Mostly upright. Color: 144B to 144C.

*Reproductive organs.*—Androecium: Stamen number: Five fused at anthers, filaments free. Anther shape: Obovate. Anther size: About 4.5 mm by 2 mm. Anther color: Apex, 11D; base, close to 53A. Amount of pollen: Moderate. Pollen color: 11C. Gynoecium: Pistil length: About 3.75 mm. Stigma color: 11C. Style color: 144C. Ovary color: 144C.

*Seed development.*—Seed development has not been observed.

Disease resistance: Plants of the new Impatiens have not been observed to be resistant to pathogens common to Impatiens.

It is claimed:

1. A new and distinct cultivar of New Guinea Impatiens plant named 'Tamar Candy Cane', as illustrated and described.

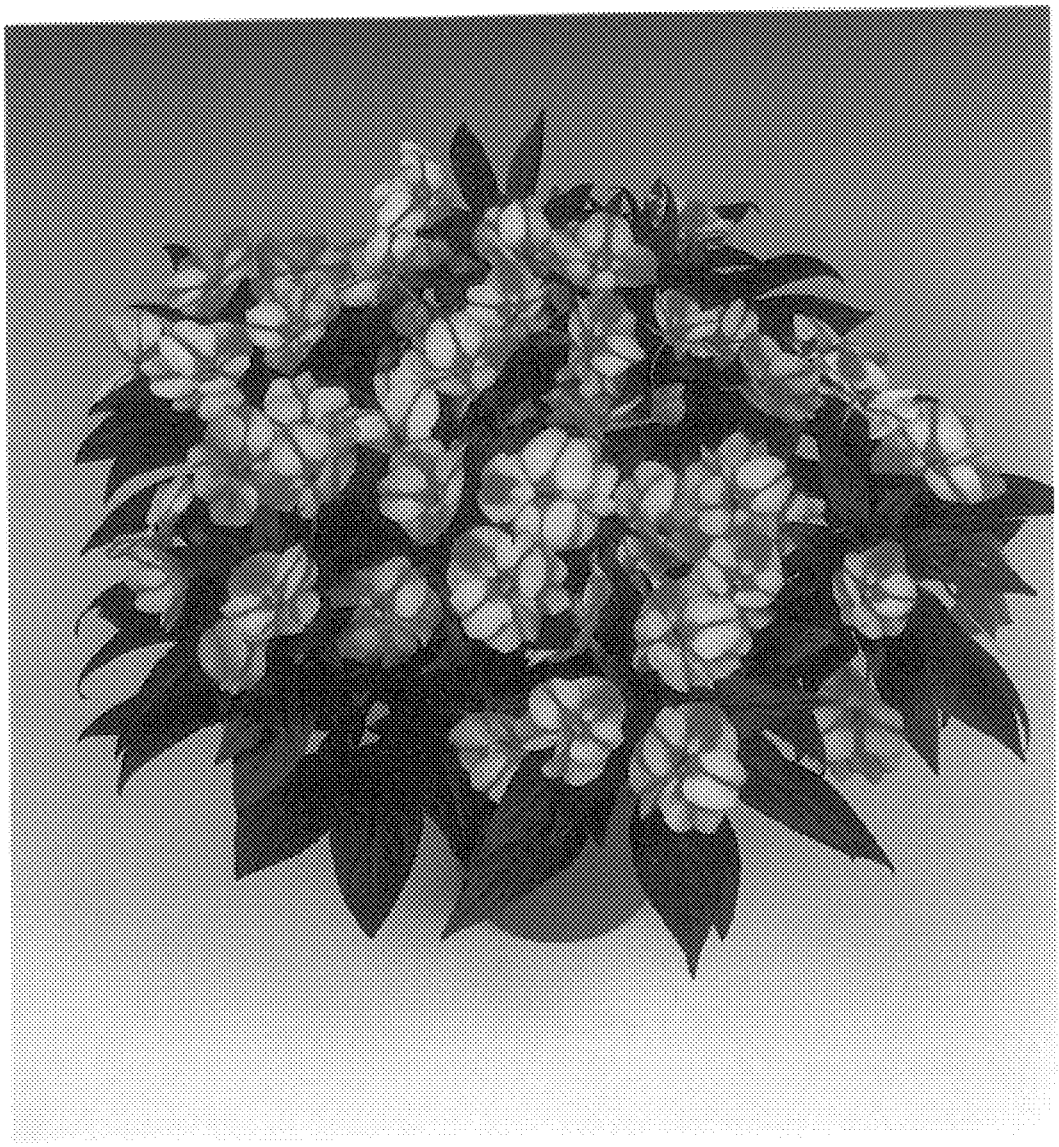

* * * * *